United States Patent
Koibuchi et al.

(10) Patent No.: US 7,087,422 B2
(45) Date of Patent: Aug. 8, 2006

(54) AMINOPEPTIDASE AND THE GENES THEREOF

(75) Inventors: Kyoko Koibuchi, Kawasaki (JP); Daiki Ninomiya, Kawasaki (JP); Mari Kojima, Kawasaki (JP); Yoichi Ueda, Kawasaki (JP); Jun-ichi Maruyama, Tokyo (JP); Katsuhiko Kitamoto, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 248 days.

(21) Appl. No.: 10/664,958

(22) Filed: Sep. 22, 2003

(65) Prior Publication Data

US 2004/0219636 A1 Nov. 4, 2004

Related U.S. Application Data

(63) Continuation of application No. PCT/JP02/02476, filed on Mar. 15, 2002.

(30) Foreign Application Priority Data

Mar. 19, 2001 (JP) .............................. 2001-078930
Sep. 26, 2001 (JP) .............................. 2001-293348

(51) Int. Cl.
*C12N 9/62* (2006.01)
*C12N 15/57* (2006.01)
*C12N 15/70* (2006.01)
*C12N 15/81* (2006.01)

(52) U.S. Cl. ................ 435/225; 435/69.1; 435/252.33; 435/254.21; 435/320.1; 536/23.2

(58) Field of Classification Search .................... None
See application file for complete search history.

(56) References Cited

FOREIGN PATENT DOCUMENTS

| DE | 195 26 485 | 1/1997 |
|----|------------|--------|
| EP | 0 359 164 | 3/1990 |
| EP | 0 794 253 | 9/1997 |
| EP | 1 036 843 | 9/2000 |
| JP | 9-294583 | 11/1997 |
| JP | 11-346777 | 12/1999 |

(Continued)

OTHER PUBLICATIONS

Seffernick, J. L., et al., 2001, "Melamine deaminase and atrazine chlorohydolase: 98 percent identical but functionally different", Journal of Bacteriology, vol. 183, No. 8, pp. 2405-2410.*

(Continued)

*Primary Examiner*—Nashaat T. Nashed
*Assistant Examiner*—William W. Moore
(74) *Attorney, Agent, or Firm*—Oblon, Spivak, McClelland, Maier & Neustadt, P.C.

(57) ABSTRACT

The object of the present invention is to provide Koji mold aminopeptidases capable of efficiently hydrolyzing persistent peptides and also genes encoding the aminopeptidases. The present invention provides *Aspergillus nidulans* aminopeptidase and nucleic acid molecules encoding it. In particular, the present invention provides a protein having an amino acid sequence represented by amino acid Nos. 1 to 519 in SEQ ID NO: 2, or a protein containing the substitution, deletion, insertion, addition or inversion of one or more amino acids in said sequence, and which protein has an activity of catalyzing the reaction for releasing an amino acid at an N-terminal of a peptide, and nucleic acid molecules encoding them.

9 Claims, 2 Drawing Sheets

FOREIGN PATENT DOCUMENTS

| | | |
|---|---|---|
| JP | 2000-325090 | 11/2000 |
| RU | 975797 | 11/1982 |
| WO | WO 96/15504 | 5/1996 |
| WO | WO 96/28542 | 9/1996 |
| WO | WO 98/14599 | 4/1998 |
| WO | WO 98/51163 | 11/1998 |
| WO | WO 98/51803 | 11/1998 |

OTHER PUBLICATIONS

S. Kunihiro, et al., "A Polymerase Chain Reaction-Based Method for Cloning Novel Members of a Gene Family Using a Combination of Degenerate and Inhibitory Primers", Gene, 289, (2002), pp. 177-184.

R. Cueva, et al., "Yeast Vacuolar Aminopeptidase YSCI Isolation and Regulation of the APE1 (LAP4) Structural Gene", Published by Elsevier Science Publishers B.V., vol. 259, No. 1, pp. 125-129, Dec. 1989.

Y. Chang, et al., Molecular Cloning and Sequencing of Genomic DNA Encoding Aminopeptidase I from *Saccharomyces cerevisiae*, The Journal of Biological Chemistry, vol. 264, No. 12, Apr. 25, 1989, pp. 6979-6983.

R. Trumbly, et al., "Isolation and Characterization of Aminopeptidase Mutants of *Saccharomyces cerevisiae*", Journal of Bacteriology, vol. 156, No. 1, Oct. 1983, pp. 36-48.

T. Nakadai, et al., "Purification and Properties of Leucine Aminopeptidase IV from *Aspergillus Oryzae*", Agric. Biol. Chem., 1977, 41(9), pp. 1657-1666.

T. Nakadai, et al., "Purification and Properties of Leucine Aminopeptidase III from *Aspergillus Oryzae*", Agr. Biol. Chem., 1973, 37 (4), pp. 775-782.

T. Nakadai, et al., "Purification and Properties of Leucine Aminopeptidase III from *Aspergillus Oryzae*", Agr. Biol., Chem. 1973, 37 (4), pp. 767-774.

T. Nakadai, et al., "Purification and Properties of Leucine Aminopeptidase I from *Aspergillus Oryzae*", Agr. Biol. Chem., 1973, 37 (4), pp. 757-765.

P. A. Vankuyk, et al., Fungal Genetics and Biology, vol. 29, pp. 201-210, "Analysis of Two *Aspergillus Nidulans* Genes Encoding Extracellular Proteases", 2000.

A. M. Blinkovsky, et al., Biochimica et Biophysica Acta, vol. 1480, pp. 171-181, "A Non-Specific Aminopeptidase from *Asperillus*", 2000.

G.-D. Lee, et al., Journal of Applied Microbiology, vol. 84, XP-002288598, pp. 561-566, "Purification and Properties of an Extracellular Leucine Aminopeptidase from the *Bacillus Sp.* N2", Sep., 1998.

\* cited by examiner

SEQUENCE LISTING

<160> NUMBER OF SEQ ID NOS: 15

<210> SEQ ID NO 1
<211> LENGTH: 3383
<212> TYPE: DNA
<213> ORGANISM: Aspergillus nidulans

<400> SEQUENCE: 1
gggagaagtg tcgcaggatc gagtgtttgt cagtgtgctg gtcacggagc cgagccaggt    60
gcatattcag attgggcctg cagcatctag agtcttgatt gcaaaggagt ccggagtaaa   120
tcactattcc gtgcctttcg acggacattc agggccggtg aggattgcga ttgtccgaca   180

-continued

| | |
|---|---|
| tggtagagaa gttaagaccg caacagggcc tgctataacg aaagagtgca cggacggtaa | 240 |
| agtaaattgg aatgcatttg taggatcaag ttaatcgata taaaattgta ctagacacta | 300 |
| aaagcgttgg gataaatggt atctagataa cttgtatgat gtttgcaata tcggggcctg | 360 |
| ttatcgccag gcccggcctc ccagccactg ataagcgtca ctcctcagtt ctccgcatga | 420 |
| ccgcatcttc cttcgctctt ctccaactct cctctctgtc gatgtcctct tcaccatctc | 480 |
| tcttgtttcc atatccttag cctttctatt gcatttttat ttatcttttg aatatggcca | 540 |
| agaaaattct gtctgacatc caccaccatg agtctaactt ggcttaccgc cagtatgccc | 600 |
| agctgcctga aaccctccac ctcaactacc agcctcctac tgctactgca accccgccg | 660 |
| cacacaccag cccgatccca gaggcaatca accccgacga ttactcgcag gcttactgcg | 720 |
| attttatgac tgagcatccc accattttc acgcagtcga tggcttctct aagcaactcg | 780 |
| aaagcaaggg atacaagtac ctatccgagc gggaattatg acgccgcag ctcaaacgcg | 840 |
| gaggaaagta ctatacgact cgcaatggaa gctcgttgat tgcgttctct gtcggccccg | 900 |
| agtataagag tgggaatggc ctcgctatca tcgccggcca cattgatgcc ctcacggcga | 960 |
| agctcaagcc cgtctcaaaa cttcccaata aagctggata cattcagatg ggagttgctc | 1020 |
| cttatgccgg cggtctgggc aagacatggt gggaccgtga tttgtctatc ggcgggaagg | 1080 |
| ttctcgttcg taacgctagc accggcaagg ttgaatccaa gctagtcaag ttgaactggc | 1140 |
| cgattgctcg catcccaacg ctagccgaac actttggcgc tccttcgcag gggccattca | 1200 |
| acaaggaaac acagatggta cctatcattg agtcgacaa ctctgatctt ttccagtcta | 1260 |
| ccactccagc ggcagacgag ggcatcgaac ccggcacctt tgcctctacg cagcccccaa | 1320 |
| aactcatcaa agtgatctcc aaggaacttg gaatcacaaa ctacagcagc attctcagct | 1380 |
| gggagctaga actttatgac agccagcctg cacgtatcgg cggtattgac aaggatttta | 1440 |
| tcttcgccgg ccgcatcgat gacaagctct gctgctacgc cgcacaggaa gccctcatgg | 1500 |
| ctacctccga ccacacctct ccctcttcca tcaagatggt cggttacttt gatgatgagg | 1560 |
| aaattggtag cttgctccgt cagggtgccc gctccaactt catgtctagc gtcatcgaac | 1620 |
| gcattgcaca atcctttgca acatcatatg gacccgatct ccttgcccaa accgttgcaa | 1680 |
| agagcttcct tatctcttct gatgtcatcc acgctgtcaa tcccaacttc ttgaatgtct | 1740 |
| atctcgagaa ccacgcgcct cgtctcaatg tcggcgtctc cgtctccgca gactcaaacg | 1800 |
| gcccacatgac taccgacagt gtcagctacg gcttcatcaa gcgcgttgct gaaaagtgcg | 1860 |
| gctctcagct gcaggtcttt caaatccgaa atgactcccg aagcggcgga accattgggc | 1920 |
| ccatgaccag ctcgcggatt ggaatgaggg ccattgatgt cggtatccca cagttgagca | 1980 |
| tgcatagcat tcgcgccacc acaggagtc gcgatcctgg gctgggtgtc aagctgttta | 2040 |
| aggggttctt tgattacttt gaagaggtgg atcgtgagtt ttctgatttt taggttgtga | 2100 |
| ctcttgtttt ctgtcgaggg gtgctgtcgc gctgcttggc cgtgtctagt ttggtttgca | 2160 |
| tgattttggt gctagggttg aagtgcttgg gcattaagaa cctcatttag aatggtgact | 2220 |
| tctttgtata cggggttcgg agtccgtcta tagaggcatg tgtaaggata aaaatcgaat | 2280 |
| cctacataat tccaggctat gcacttgaac agacaacatc tagattctag gcacgtcaaa | 2340 |
| ccatacaata tattaagagg cttccgtcta tttgatgctc cacccggcac gaatctcaac | 2400 |
| agtaagcccc gtagtctact ccgtacttct tgcctgccga aggagaggat ggagatgagg | 2460 |
| gtgacgaatg cgttgttttc accagtgccc caatgacagt tgcattatcc tcaatttaat | 2520 |
| cagccccgtc tccttccagt tccaccccag cctttggagc agtccgggca atgctctctg | 2580 |

-continued

```
cgacacttac tgtcatgatc ccctacata aacacacggc ttcgcagccc cagccccagc    2640
cccattcagg gccaaaagct ctagactgat ccgcatccca ctcacaactc ccatgttcca    2700
aatcattgat gtgcgttgtg attgtagtag aaatgcccat tcccccaatg ctccagaaaa    2760
ctggcggccg gggttcttgc ccaactgtaa gcgctaggct ccgagataat ctcttagact    2820
tggatttcga tctggatctg gggttgctgt gcgatgagag gagttgtgga atcatacggg    2880
aaagcagggg ccgcagagtc ggtaggcagg cgcagactat gccgacgttg cattccactg    2940
cggaccaggt tgcggcaccg acgttgtcat ctgcttgtcg ttagtagggg ttttttttggg    3000 ttgatggagg gacgtacagg ttgggtccga agagtcagcg attctttta gggacatcaa    3060 acggcaaatg cttgttatgc agacgctaga attactcagg attagcagat gcacacaccg    3120
accatggaac agaaaacgta caaaccccc accgcaaaaa ttgcaataag agcaactctc    3180
tgcttccttg gcaaatcaag actatacaag gcaggtatag ggataactag gatagcaagg    3240
tccgtcgcaa tatgcattga agcattggag aaccacagag ccttcgaact gagacatgat    3300
cccgggattg ttgggtccca gaaacgtgct actggtatgc agttcaagaa cccgctaagc    3360
acagcccatg tgccgattga cga                                          3383
```

```
<210> SEQ ID NO 2
<211> LENGTH: 1916
<212> TYPE: DNA
<213> ORGANISM: Aspergillus nidulans
<220> FEATURE:
<221> NAME/KEY: CDS
<222> LOCATION: (72)..(1628)

<400> SEQUENCE: 2
```

```
tgtcctcttc accatctctc ttgtttccat atccttagcc tttctattgc attttattt     60 atcttttgaa t atg gcc aag aaa att ctg tct gac atc cac cac cat gag    110
            Met Ala Lys Lys Ile Leu Ser Asp Ile His His His Glu
              1               5                   10 tct aac ttg gct tac cgc cag tat gcc cag ctg cct gaa acc ctc cac    158
Ser Asn Leu Ala Tyr Arg Gln Tyr Ala Gln Leu Pro Glu Thr Leu His
 15                  20                  25 ctc aac tac cag cct cct act gct act gca acc ccc gcc gca cac acc    206
Leu Asn Tyr Gln Pro Pro Thr Ala Thr Ala Thr Pro Ala Ala His Thr
 30                  35                  40                  45 agc ccg atc cca gag gca atc aac ccc gac gat tac tcg cag gct tac    254
Ser Pro Ile Pro Glu Ala Ile Asn Pro Asp Asp Tyr Ser Gln Ala Tyr
                 50                  55                  60 tgc gat ttt atg act gag cat ccc acc att ttt cac gca gtc gat ggc    302
Cys Asp Phe Met Thr Glu His Pro Thr Ile Phe His Ala Val Asp Gly
             65                  70                  75 ttc tct aag caa ctc gaa agc aag gga tac aag tac cta tcc gag cgg    350
Phe Ser Lys Gln Leu Glu Ser Lys Gly Tyr Lys Tyr Leu Ser Glu Arg
         80                  85                  90 gaa tta tgg acg ccg cag ctc aaa cgc gga gga aag tac tat acg act    398
Glu Leu Trp Thr Pro Gln Leu Lys Arg Gly Gly Lys Tyr Tyr Thr Thr
     95                 100                 105 cgc aat gga agc tcg ttg att gcg ttc tct gtc ggc ccc gag tat aag    446
Arg Asn Gly Ser Ser Leu Ile Ala Phe Ser Val Gly Pro Glu Tyr Lys
110                 115                 120                 125 agt ggg aat ggc ctc gct atc atc gcc ggc cac att gat gcc ctc acg    494
Ser Gly Asn Gly Leu Ala Ile Ile Ala Gly His Ile Asp Ala Leu Thr
                130                 135                 140 gcg aag ctc aag ccc gtc tca aaa ctt ccc aat aaa gct gga tac att    542
```

-continued

| | | |
|---|---|---|
| Ala Lys Leu Lys Pro Val Ser Lys Leu Pro Asn Lys Ala Gly Tyr Ile<br>     145                    150                   155 | |

```
cag atg gga gtt gct cct tat gcc ggc ggt ctg ggc aag aca tgg tgg      590
Gln Met Gly Val Ala Pro Tyr Ala Gly Gly Leu Gly Lys Thr Trp Trp
        160                 165                 170 gac cgt gat ttg tct atc ggc ggg aag gtt ctc gtt cgt aac gct agc      638
Asp Arg Asp Leu Ser Ile Gly Gly Lys Val Leu Val Arg Asn Ala Ser
175                 180                 185 acc ggc aag gtt gaa tcc aag cta gtc aag ttg aac tgg ccg att gct      686
Thr Gly Lys Val Glu Ser Lys Leu Val Lys Leu Asn Trp Pro Ile Ala
190                 195                 200                 205 cgc atc cca acg cta gcc gaa cac ttt ggc gct cct tcg cag ggg cca      734
Arg Ile Pro Thr Leu Ala Glu His Phe Gly Ala Pro Ser Gln Gly Pro
            210                 215                 220 ttc aac aag gaa aca cag atg gta cct atc att gga gtc gac aac tct      782
Phe Asn Lys Glu Thr Gln Met Val Pro Ile Ile Gly Val Asp Asn Ser
                225                 230                 235 gat ctt ttc cag tct acc act cca gcg gca gac gag ggc atc gaa ccc      830
Asp Leu Phe Gln Ser Thr Thr Pro Ala Ala Asp Glu Gly Ile Glu Pro
        240                 245                 250 ggc acc ttt gcc tct acg cag ccc cca aaa ctc atc aaa gtg atc tcc      878
Gly Thr Phe Ala Ser Thr Gln Pro Pro Lys Leu Ile Lys Val Ile Ser
255                 260                 265 aag gaa ctt gga atc aca aac tac agc agc att ctc agc tgg gag cta      926
Lys Glu Leu Gly Ile Thr Asn Tyr Ser Ser Ile Leu Ser Trp Glu Leu
270                 275                 280                 285 gaa ctt tat gac agc cag cct gca cgt atc ggc ggt att gac aag gat      974
Glu Leu Tyr Asp Ser Gln Pro Ala Arg Ile Gly Gly Ile Asp Lys Asp
            290                 295                 300 ttt atc ttc gcc ggc cgc atc gat gac aag ctc tgc tgc tac gcc gca     1022
Phe Ile Phe Ala Gly Arg Ile Asp Asp Lys Leu Cys Cys Tyr Ala Ala
                305                 310                 315 cag gaa gcc ctc atg gct acc tcc gac cac acc tct ccc tct tcc atc     1070
Gln Glu Ala Leu Met Ala Thr Ser Asp His Thr Ser Pro Ser Ser Ile
        320                 325                 330 aag atg gtc ggt tac ttt gat gat gag gaa att ggt agc ttg ctc cgt     1118
Lys Met Val Gly Tyr Phe Asp Asp Glu Glu Ile Gly Ser Leu Leu Arg
335                 340                 345 cag ggt gcc cgc tcc aac ttc atg tct agc gtc atc gaa cgc att gca     1166
Gln Gly Ala Arg Ser Asn Phe Met Ser Ser Val Ile Glu Arg Ile Ala
350                 355                 360                 365 caa tcc ttt gca aca tca tat gga ccc gat ctc ctt gcc caa acc gtt     1214
Gln Ser Phe Ala Thr Ser Tyr Gly Pro Asp Leu Leu Ala Gln Thr Val
            370                 375                 380 gca aag agc ttc ctt atc tct tct gat gtc atc cac gct gtc aat ccc     1262
Ala Lys Ser Phe Leu Ile Ser Ser Asp Val Ile His Ala Val Asn Pro
                385                 390                 395 aac ttc ttg aat gtc tat ctc gag aac cac gcg cct cgt ctc aat gtc     1310
Asn Phe Leu Asn Val Tyr Leu Glu Asn His Ala Pro Arg Leu Asn Val
        400                 405                 410 ggc gtc tcc gtc tcc gca gac tca aac ggc cac atg act acc gac agt     1358
Gly Val Ser Val Ser Ala Asp Ser Asn Gly His Met Thr Thr Asp Ser
415                 420                 425 gtc agc tac ggc ttc atc aag cgc gtt gct gaa aag tgc ggc tct cag     1406
Val Ser Tyr Gly Phe Ile Lys Arg Val Ala Glu Lys Cys Gly Ser Gln
430                 435                 440                 445 ctg cag gtc ttt caa atc cga aat gac tcc cga agc ggc gga acc att     1454
Leu Gln Val Phe Gln Ile Arg Asn Asp Ser Arg Ser Gly Gly Thr Ile
            450                 455                 460
```

-continued

```
ggg ccc atg acc agc tcg cgg att gga atg agg gcc att gat gtc ggt    1502
Gly Pro Met Thr Ser Ser Arg Ile Gly Met Arg Ala Ile Asp Val Gly
        465                 470                 475 atc cca cag ttg agc atg cat agc att cgc gcc acc aca ggg agt cgc    1550
Ile Pro Gln Leu Ser Met His Ser Ile Arg Ala Thr Thr Gly Ser Arg
480                 485                 490 gat cct ggg ctg ggt gtc aag ctg ttt aag ggg ttc ttt gat tac ttt    1598
Asp Pro Gly Leu Gly Val Lys Leu Phe Lys Gly Phe Phe Asp Tyr Phe
    495                 500                 505 gaa gag gtg gat cgt gag ttt tct gat ttt taggttgtga ctcttgtttt      1648
Glu Glu Val Asp Arg Glu Phe Ser Asp Phe
510                 515 ctgtcgaggg gtgctgtcgc gctgcttggc cgtgtctagt ttggtttgca tgattttggt    1708
gctagggttg aagtgcttgg gcattaagaa cctcatttag aatggtgact tctttgtata    1768
cggggttcgg agtccgtcta tagaggcatg tgtaaggata aaaatcgaat cctacataat    1828
tccaggctat gcacttgaac agacaacatc tagattctag gcacgtcaaa ccatacaata    1888
tattaagagg cttccgtcta tttgatgc                                      1916
```

<210> SEQ ID NO 3
<211> LENGTH: 519
<212> TYPE: PRT
<213> ORGANISM: Aspergillus nidulans

<400> SEQUENCE: 3

```
Met Ala Lys Lys Ile Leu Ser Asp Ile His His Glu Ser Asn Leu
1               5                   10                  15

Ala Tyr Arg Gln Tyr Ala Gln Leu Pro Glu Thr Leu His Leu Asn Tyr
            20                  25                  30

Gln Pro Pro Thr Ala Thr Ala Thr Pro Ala Ala His Thr Ser Pro Ile
        35                  40                  45

Pro Glu Ala Ile Asn Pro Asp Asp Tyr Ser Gln Ala Tyr Cys Asp Phe
    50                  55                  60

Met Thr Glu His Pro Thr Ile Phe His Ala Val Asp Gly Phe Ser Lys
65                  70                  75                  80

Gln Leu Glu Ser Lys Gly Tyr Lys Tyr Leu Ser Glu Arg Glu Leu Trp
                85                  90                  95

Thr Pro Gln Leu Lys Arg Gly Gly Lys Tyr Tyr Thr Thr Arg Asn Gly
            100                 105                 110

Ser Ser Leu Ile Ala Phe Ser Val Gly Pro Glu Tyr Lys Ser Gly Asn
        115                 120                 125

Gly Leu Ala Ile Ile Ala Gly His Ile Asp Ala Leu Thr Ala Lys Leu
    130                 135                 140

Lys Pro Val Ser Lys Leu Pro Asn Lys Ala Gly Tyr Ile Gln Met Gly
145                 150                 155                 160

Val Ala Pro Tyr Ala Gly Gly Leu Gly Lys Thr Trp Trp Asp Arg Asp
                165                 170                 175

Leu Ser Ile Gly Gly Lys Val Leu Val Arg Asn Ala Ser Thr Gly Lys
            180                 185                 190

Val Glu Ser Lys Leu Val Lys Leu Asn Trp Pro Ile Ala Arg Ile Pro
        195                 200                 205

Thr Leu Ala Glu His Phe Gly Ala Pro Ser Gln Gly Pro Phe Asn Lys
    210                 215                 220

Glu Thr Gln Met Val Pro Ile Ile Gly Val Asp Asn Ser Asp Leu Phe
225                 230                 235                 240
```

```
Gln Ser Thr Thr Pro Ala Ala Asp Glu Gly Ile Glu Pro Gly Thr Phe
            245                 250                 255

Ala Ser Thr Gln Pro Pro Lys Leu Ile Lys Val Ile Ser Lys Glu Leu
            260                 265                 270

Gly Ile Thr Asn Tyr Ser Ser Ile Leu Ser Trp Glu Leu Glu Leu Tyr
            275                 280                 285

Asp Ser Gln Pro Ala Arg Ile Gly Ile Asp Lys Asp Phe Ile Phe
        290                 295                 300

Ala Gly Arg Ile Asp Asp Lys Leu Cys Cys Tyr Ala Ala Gln Glu Ala
305                 310                 315                 320

Leu Met Ala Thr Ser Asp His Thr Ser Pro Ser Ser Ile Lys Met Val
            325                 330                 335

Gly Tyr Phe Asp Asp Glu Glu Ile Gly Ser Leu Leu Arg Gln Gly Ala
            340                 345                 350

Arg Ser Asn Phe Met Ser Ser Val Ile Glu Arg Ile Ala Gln Ser Phe
            355                 360                 365

Ala Thr Ser Tyr Gly Pro Asp Leu Leu Ala Gln Thr Val Ala Lys Ser
        370                 375                 380

Phe Leu Ile Ser Ser Asp Val Ile His Ala Val Asn Pro Asn Phe Leu
385                 390                 395                 400

Asn Val Tyr Leu Glu Asn His Ala Pro Arg Leu Asn Val Gly Val Ser
            405                 410                 415

Val Ser Ala Asp Ser Asn Gly His Met Thr Thr Asp Ser Val Ser Tyr
            420                 425                 430

Gly Phe Ile Lys Arg Val Ala Glu Lys Cys Gly Ser Gln Leu Gln Val
            435                 440                 445

Phe Gln Ile Arg Asn Asp Ser Arg Ser Gly Gly Thr Ile Gly Pro Met
        450                 455                 460

Thr Ser Ser Arg Ile Gly Met Arg Ala Ile Asp Val Gly Ile Pro Gln
465                 470                 475                 480

Leu Ser Met His Ser Ile Arg Ala Thr Thr Gly Ser Arg Asp Pro Gly
            485                 490                 495

Leu Gly Val Lys Leu Phe Lys Gly Phe Phe Asp Tyr Phe Glu Glu Val
            500                 505                 510

Asp Arg Glu Phe Ser Asp Phe
        515

<210> SEQ ID NO 4
<211> LENGTH: 1679
<212> TYPE: DNA
<213> ORGANISM: Aspergillus oryzae
<220> FEATURE:
<221> NAME/KEY: CDS
<222> LOCATION: (73)..(1602)

<400> SEQUENCE: 4
caggcttaaa ccgcattccg acaagatatc tagcctttaa actaagaaat tttccaactc      60
ctagccttcg ac atg acc aaa agg agt gtc ctt gat ctc cgt gat tct gcc    111
              Met Thr Lys Arg Ser Val Leu Asp Leu Arg Asp Ser Ala
                1               5                  10 atg gct tat cgc ctg tcg gcc cag ctt cct gag ccc tcc cca gcc acc    159
Met Ala Tyr Arg Leu Ser Ala Gln Leu Pro Glu Pro Ser Pro Ala Thr
         15                 20                  25 att gca acc cca gtg gcg agg agt ggc ccc ttc gcc ccg gaa gat tac    207
Ile Ala Thr Pro Val Ala Arg Ser Gly Pro Phe Ala Pro Glu Asp Tyr
30              35                  40                  45
```

```
acg aaa cca tac tgc gaa ttc atg aca gca aac ccc aca atc ttt cac      255
Thr Lys Pro Tyr Cys Glu Phe Met Thr Ala Asn Pro Thr Ile Phe His
             50                  55                  60 gcc gtt gat ggt ttc acc agg cag ctc gaa agc cag gga tac aag cgc      303
Ala Val Asp Gly Phe Thr Arg Gln Leu Glu Ser Gln Gly Tyr Lys Arg
             65                  70                  75 ctt ccc gag cgc gag acg tgg aac tcc aag tta gag aag ggt ggg aag      351
Leu Pro Glu Arg Glu Thr Trp Asn Ser Lys Leu Glu Lys Gly Gly Lys
         80                  85                  90 tac tac gtc act cgg aat ggt agt gct ttc atc tca ttc tca att gga      399
Tyr Tyr Val Thr Arg Asn Gly Ser Ala Phe Ile Ser Phe Ser Ile Gly
         95                 100                 105 aga gat tat aaa agt ggc aat gga atg gcc att gtt gca ggt cat atc      447
Arg Asp Tyr Lys Ser Gly Asn Gly Met Ala Ile Val Ala Gly His Ile
110                 115                 120                 125 gat gca ctc acc gcc aaa ttg aag ccc gtg tcc aag ctg ccc aac aag      495
Asp Ala Leu Thr Ala Lys Leu Lys Pro Val Ser Lys Leu Pro Asn Lys
                130                 135                 140 gct ggc ttt tcc cag ctc gga gtt gcg ccc tac gca ggc gct ctg agt      543
Ala Gly Phe Ser Gln Leu Gly Val Ala Pro Tyr Ala Gly Ala Leu Ser
            145                 150                 155 gac aca tgg tgg gac cgc gat ctc tca ata ggt ggc cgt gtt ctg gtc      591
Asp Thr Trp Trp Asp Arg Asp Leu Ser Ile Gly Gly Arg Val Leu Val
            160                 165                 170 caa gac tcc aac acc ggg aaa gtc gag tcc aaa tta gtc aaa ttg gac      639
Gln Asp Ser Asn Thr Gly Lys Val Glu Ser Lys Leu Val Lys Leu Asp
175                 180                 185 tgg ccc att gct cgg atc cca acc ctg gca cct cat ttc ggg gct ccc      687
Trp Pro Ile Ala Arg Ile Pro Thr Leu Ala Pro His Phe Gly Ala Pro
190                 195                 200                 205 tcg caa ggc ccc ttc aac aaa gag act cag atg gtg cct ata att ggc      735
Ser Gln Gly Pro Phe Asn Lys Glu Thr Gln Met Val Pro Ile Ile Gly
                210                 215                 220 gtt gat aac tcc gat ctt ttc cag cag caa gcc cca tcc aag ata gat      783
Val Asp Asn Ser Asp Leu Phe Gln Gln Gln Ala Pro Ser Lys Ile Asp
            225                 230                 235 caa gac aac ggg atc aaa cct ggt aca ttt gca gcc acg caa ccg gaa      831
Gln Asp Asn Gly Ile Lys Pro Gly Thr Phe Ala Ala Thr Gln Pro Glu
            240                 245                 250 aag ctt gtc aaa gtc ata tcc aag gag ctt ggt atc aca gac tac agc      879
Lys Leu Val Lys Val Ile Ser Lys Glu Leu Gly Ile Thr Asp Tyr Ser
            255                 260                 265 tcg att ata agc tgg gag ctg gag ctg tat gac agt caa cca gca caa      927
Ser Ile Ile Ser Trp Glu Leu Glu Leu Tyr Asp Ser Gln Pro Ala Gln
270                 275                 280                 285 gtt ggt ggc ctg gac aag gac ctg att ttt gct ggt cgc att gac gat      975
Val Gly Gly Leu Asp Lys Asp Leu Ile Phe Ala Gly Arg Ile Asp Asp
                290                 295                 300 aag ctc tgc tgc tat gcc gct cag gaa gct ctg ctt gcc tca tcc gac     1023
Lys Leu Cys Cys Tyr Ala Ala Gln Glu Ala Leu Leu Ala Ser Ser Asp
            305                 310                 315 agt act tca act agc tct atc aag atg gtc ggt atg ttt gat gac gag     1071
Ser Thr Ser Thr Ser Ser Ile Lys Met Val Gly Met Phe Asp Asp Glu
            320                 325                 330 gaa att gga agc ctg ctt cgc cag gga gct cga tcc aac ttc atg agc     1119
Glu Ile Gly Ser Leu Leu Arg Gln Gly Ala Arg Ser Asn Phe Met Ser
            335                 340                 345 agt gtc ata gag cgt att acg gaa gcc ttc tca ccc aat tac ggt cct     1167
Ser Val Ile Glu Arg Ile Thr Glu Ala Phe Ser Pro Asn Tyr Gly Pro
350                 355                 360                 365
```

```
aac gtg ctg tct caa act gtg gcg aac agc ttc ttc gtg tct tcg gac    1215
Asn Val Leu Ser Gln Thr Val Ala Asn Ser Phe Phe Val Ser Ser Asp
                370                 375                 380 gtc atc cat gcg gtc aat ccg aac ttc ctt ggt gtc tat ctt gag aac    1263
Val Ile His Ala Val Asn Pro Asn Phe Leu Gly Val Tyr Leu Glu Asn
            385                 390                 395 cat gct ccc cgt ctg aac gtc ggt gtg gcc gtc tcg gct gac tct aac    1311
His Ala Pro Arg Leu Asn Val Gly Val Ala Val Ser Ala Asp Ser Asn
        400                 405                 410 ggc cat atg aca aca gac agt gtg agc tac gga ttc atc aag cgt gtc    1359
Gly His Met Thr Thr Asp Ser Val Ser Tyr Gly Phe Ile Lys Arg Val
    415                 420                 425 gct gat cga tgt ggc tcg acc ttg cag gtc ttc cag att cgt aat gac    1407
Ala Asp Arg Cys Gly Ser Thr Leu Gln Val Phe Gln Ile Arg Asn Asp
430                 435                 440                 445 tcc cgt agt ggc ggg act att gga ccc atg acc agt tct cgc att ggc    1455
Ser Arg Ser Gly Gly Thr Ile Gly Pro Met Thr Ser Ser Arg Ile Gly
                450                 455                 460 atg agg gcc att gac gtg ggg atc ccg cag ttg agt atg cac agt atc    1503
Met Arg Ala Ile Asp Val Gly Ile Pro Gln Leu Ser Met His Ser Ile
            465                 470                 475 cgt gcg act acc ggt agt ttg gat ccg gga ttg ggt gtg aag ctg ttc    1551
Arg Ala Thr Thr Gly Ser Leu Asp Pro Gly Leu Gly Val Lys Leu Phe
        480                 485                 490 aag ggc ttt ttc gac tat ttc gag gag gtg gac aag gaa ttt gca gat    1599
Lys Gly Phe Phe Asp Tyr Phe Glu Glu Val Asp Lys Glu Phe Ala Asp
    495                 500                 505 ttc tgatgcgctc ctctggaata ctaggaaatg tttccatcga taagtatgca         1652
Phe
510 ctatctggga ttccgatgtt ggatctg                                      1679

<210> SEQ ID NO 5
<211> LENGTH: 510
<212> TYPE: PRT
<213> ORGANISM: Aspergillus oryzae

<400> SEQUENCE: 5

Met Thr Lys Arg Ser Val Leu Asp Leu Arg Asp Ser Ala Met Ala Tyr
1               5                   10                  15

Arg Leu Ser Ala Gln Leu Pro Glu Pro Ser Pro Ala Thr Ile Ala Thr
            20                  25                  30

Pro Val Ala Arg Ser Gly Pro Phe Ala Pro Glu Asp Tyr Thr Lys Pro
        35                  40                  45

Tyr Cys Glu Phe Met Thr Ala Asn Pro Thr Ile Phe His Ala Val Asp
    50                  55                  60

Gly Phe Thr Arg Gln Leu Glu Ser Gln Gly Tyr Lys Arg Leu Pro Glu
65                  70                  75                  80

Arg Glu Thr Trp Asn Ser Lys Leu Glu Lys Gly Gly Lys Tyr Tyr Val
                85                  90                  95

Thr Arg Asn Gly Ser Ala Phe Ile Phe Ser Ile Gly Arg Asp Tyr
            100                 105                 110

Lys Ser Gly Asn Gly Met Ala Ile Val Ala Gly His Ile Asp Ala Leu
        115                 120                 125

Thr Ala Lys Leu Lys Pro Val Ser Lys Leu Pro Asn Lys Ala Gly Phe
    130                 135                 140

Ser Gln Leu Gly Val Ala Pro Tyr Ala Gly Ala Leu Ser Asp Thr Trp
```

-continued

```
            145                 150                 155                 160
        Trp Asp Arg Asp Leu Ser Ile Gly Gly Arg Val Leu Val Gln Asp Ser
                        165                 170                 175

Asn Thr Gly Lys Val Glu Ser Lys Leu Val Lys Leu Asp Trp Pro Ile
                        180                 185                 190

Ala Arg Ile Pro Thr Leu Ala Pro His Phe Gly Ala Pro Ser Gln Gly
                        195                 200                 205

Pro Phe Asn Lys Glu Thr Gln Met Val Pro Ile Ile Gly Val Asp Asn
                        210                 215                 220

Ser Asp Leu Phe Gln Gln Gln Ala Pro Ser Lys Ile Asp Gln Asp Asn
        225                 230                 235                 240

Gly Ile Lys Pro Gly Thr Phe Ala Ala Thr Gln Pro Glu Lys Leu Val
                        245                 250                 255

Lys Val Ile Ser Lys Glu Leu Gly Ile Thr Asp Tyr Ser Ser Ile Ile
                        260                 265                 270

Ser Trp Glu Leu Glu Leu Tyr Asp Ser Gln Pro Ala Gln Val Gly Gly
                        275                 280                 285

Leu Asp Lys Asp Leu Ile Phe Ala Gly Arg Ile Asp Asp Lys Leu Cys
                        290                 295                 300

Cys Tyr Ala Ala Gln Glu Ala Leu Leu Ala Ser Ser Asp Ser Thr Ser
        305                 310                 315                 320

Thr Ser Ser Ile Lys Met Val Gly Met Phe Asp Glu Glu Ile Gly
                        325                 330                 335

Ser Leu Leu Arg Gln Gly Ala Arg Ser Asn Phe Met Ser Ser Val Ile
                        340                 345                 350

Glu Arg Ile Thr Glu Ala Phe Ser Pro Asn Tyr Gly Pro Asn Val Leu
                        355                 360                 365

Ser Gln Thr Val Ala Asn Ser Phe Phe Val Ser Ser Asp Val Ile His
            370                 375                 380

Ala Val Asn Pro Asn Phe Leu Gly Val Tyr Leu Glu Asn His Ala Pro
        385                 390                 395                 400

Arg Leu Asn Val Gly Val Ala Val Ser Ala Asp Ser Asn Gly His Met
                        405                 410                 415

Thr Thr Asp Ser Val Ser Tyr Gly Phe Ile Lys Arg Val Ala Asp Arg
                        420                 425                 430

Cys Gly Ser Thr Leu Gln Val Phe Gln Ile Arg Asn Asp Ser Arg Ser
                        435                 440                 445

Gly Gly Thr Ile Gly Pro Met Thr Ser Ser Arg Ile Gly Met Arg Ala
                        450                 455                 460

Ile Asp Val Gly Ile Pro Gln Leu Ser Met His Ser Ile Arg Ala Thr
        465                 470                 475                 480

Thr Gly Ser Leu Asp Pro Gly Leu Gly Val Lys Leu Phe Lys Gly Phe
                        485                 490                 495

Phe Asp Tyr Phe Glu Glu Val Asp Lys Glu Phe Ala Asp Phe
                        500                 505                 510
```

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
ctcaaacggc cacatgacta c                                        21

<210> SEQ ID NO 7
<211> LENGTH: 22
<212> TYPE: DNA
<213> ORGANISM: Artificial Sequence
<220> FEATURE:
<223> OTHER INFORMATION: Synthetic DNA

<400> SEQUENCE: 7
gtctgttcaa gtgcatagcc tg                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8
caccaccatg agtctaactt gg                                          22

<210> SEQ ID NO 9
<211> LENGTH: 22
<212> TYPE: DNA
<213> ORGANISM: Artificial Sequence
<220> FEATURE:
<223> OTHER INFORMATION: Synthetic DNA

<400> SEQUENCE: 9
gtctgttcaa gtgcatagcc tg                                          22

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
cgtggtacca tggtctagag t                                           21

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
aatcgcagta agcctgcgag                                             20

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
cgtggtacca tggtctagag t                                           21

<210> SEQ ID NO 13
<211> LENGTH: 20
<212> TYPE: DNA
<213> ORGANISM: Artificial Sequence
<220> FEATURE:

-continued

```
<223> OTHER INFORMATION: Synthetic DNA

<400> SEQUENCE: 13
catgggccca atggttccgc                                              20

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
ccagattcgt aatgactccc g                                            21

<210> SEQ ID NO 15
<211> LENGTH: 32
<212> TYPE: DNA
<213> ORGANISM: Artificial Sequence
<220> FEATURE:
<223> OTHER INFORMATION: Synthetic DNA

<400> SEQUENCE: 15
ctactactac taggccacgc gtcgactagt ac                                32
```

AMINOPEPTIDASE AND THE GENES THEREOF

CROSS-REFERENCE TO RELATED APPLICATIONS

The present application is a continuation of PCT/JP02/02476 filed on Mar. 15, 2002, which claims priority to JP 2001-078930, filed on Mar. 19, 2001, and to JP 2001-293348, filed on Sep. 26, 2001.

BACKGROUND OF THE INVENTION

The present invention relates to aminopeptidases and genes encoding them.

Koji molds are used for the preparation of soy sauce, miso (fermented soybean paste) and other natural seasonings containing protein hydrolysates. For example, soy sauce is produced in two steps, i. e. a step of preparing koji and fermentation step. The starting materials are hydrolyzed by an enzyme produced by a koji mold (a filamentous fungus belonging to the genus *Aspergillus*) in the step of preparing the koji mold. For improving the taste of the soy sauce, it is important to increase the amount of free amino acids in soy sauce in these steps.

Amino acids are produced from the starting protein by two steps. The first step is the release of peptides from proteins by proteases and the second step is the production of amino acids through hydrolysis of peptides, catalyzed by peptidases.

As for peptidases of koji mold, those derived from *Aspergillus oryzae* and *Aspergillus sojae* were reported (JP-Kokai No. 11-346777, DE 95-1952648, WO 9851163, WO 9628542, WO 9615504, WO 9851803 and WO 9814599). It is described therein that leucine aminopeptidase is particularly important in the preparation of soy sauce. However, it has not been reported that known leucine aminopeptidase is resistant to salt. As for the genes of leucine aminopeptidase of the genus *Aspergillus*, Kaifu et al. reported *Aspergillus sojae* (JP-Kokai No. 11-346777), but there has been no report on the salt-resistance of this enzyme.

As for the genus *Bacillus*, there is a reported of salt-resistant leucine aminopeptidase (Lee, G. D. et al., J. Appl. Microbiol. (1988), 85 (3)).

On the other hand, Asano et al. noted that storage proteins in soybean are hydrolyzed into amino acids in a very short period of time in the course of the germination thereof. They found peptidases (aminopeptidase GX capable of efficiently hydrolyzing acidic amino acid-containing peptides and leucine aminopeptidases) in soybean cotyledons and succeeded in effectively hydrolyzing soybean protein (JP-Kokai No. Hei 9-294583).

In view of the enzymologic properties of aminopeptidase GX of soybean, aminopeptidase GX was a new aminopeptidase that had never been reported. The presence of the aminopeptidase GX of soybean had not been known except in germinating soybean. Aminopeptidase GX of soybean has an activity of effectively releasing N-terminal acidic amino acids from peptides having acidic amino acids such as glutamic acid at the N-terminal thereof. Accordingly, it is possible to produce soy sauce having a high free glutamic acid content and an excellent taste, taking advantage of the effect of this enzyme.

Ninomiya et al. succeeded in producing a large amount of soybean aminopeptidase GX by a genetic recombination technique (JP-Kokai No. 2000-325090). However, it is difficult to use aminopeptidase GX of soybean produced by this method for the production of soy sauce because of the problems of GMO and costs.

SUMMARY OF THE INVENTION

The object of the present invention is to provide an aminopeptidase derived from koji molds, which is effective in producing soy sauce or protein hydrolysates having a high free amino acid content and an excellent seasoning property, and also a gene encoding the aminopeptidase.

After intensive investigations made for the purpose of solving the above-described problems, the inventors have succeeded in obtaining DNA encoding a new aminopeptidase from *Aspergillus nidulans* by screening the genome DNA library of *Aspergillus nidulans* with *A. nidulans* EST homologous to soybean aminopeptidase GX genes as the probe. The present invention has been completed on the basis of this fact.

Namely, the present invention provides a protein of any of the following items (A) to (D):

(A) a protein having the amino acid sequence represented by amino acid Nos. 1 to 519 in SEQ ID NO: 2, (B) a protein having the amino acid sequence represented by amino acid Nos. 1 to 510 in SEQ ID NO: 4, (C) a protein having the amino acid sequence corresponding to amino acid Nos. 1 to 519 in SEQ ID NO: 2, wherein one or more amino acid(s) are substituted, deleted, inserted, added or inverted in the sequence of SEQ ID NO:2, and which protein has an activity of catalyzing the reaction for releasing an amino acid from the N-terminal of a peptide, or (D) a protein having an amino acid sequence corresponding to amino acid Nos. 1 to 510 in SEQ ID NO: 4, wherein one or more amino acid(s) are substituted, deleted, inserted, added or inverted in the sequence of SEQ ID:4, and which protein has an activity of catalyzing the reaction for releasing an amino acid from the N-terminal of a peptide, The present invention also provides nucleic acid molecules encoding any of the aforementioned proteins (A) to (D), recombinant nucleic acid molecules containing these nucleic acid molecules, transformed microorganism hosts and a process for producing an aminopeptidase by using the transformed microorganism hosts. In the present invention, the transformed microorganism hosts include transformed filamentous fungi, in particular, transformed koji molds.

The present invention further provides an aminopeptidase having the following properties 1) to 8):

1) The aminopeptidase hydrolyzes a peptide or protein having leucine or methionine at the N-terminal to release leucine or methionine;

2) The aminopeptidase has an optimum pH of about 7.0 to 7.5;

3) The aminopeptidase has an optimum temperature of about 37 to 45° C.;

4) The aminopeptidase has a remaining activity of at least 80% even at a sodium chloride concentration of 3 M, when the activity thereof in the absence of sodium chloride is defined as 100%;

5) The aminopeptidase has a remaining activity of at least 80% after the storage in the presence of 3 M of sodium chloride at 0° C. for 24 hours, when the activity thereof after the storage in the absence of sodium chloride at 0° C. for 24 hours is defined as 100%;

6) The aminopeptidase has a remaining activity of at least 60% after the storage at pH 5.8 to 9.5 at 0° C. for 24 hours, while the activity thereof after the storage at pH 7.5 at 0° C. for 24 hours is defined as 100%;
7) The aminopeptidase shows a molecular weight of about 550 kD as measured by native PAGE and a molecular weight of 22 or 33 kD as measured by SDS-PAGE after reducing and heating; and,
8) The aminopeptidase requires cobalt ion or zinc ion for the activation.

DESCRIPTION OF THE PREFERRED EMBODIMENTS

Figure 1:
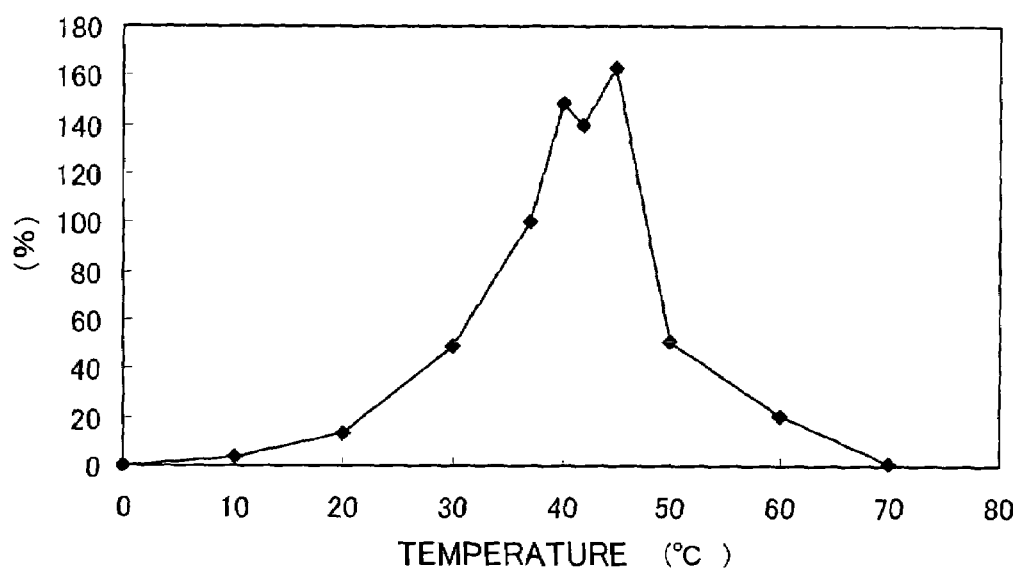
FIG. 1 is a graph showing the temperature-dependency of PepE activity. The horizontal axis represents the temperature, and the longitudinal axis represents the relative activity of leucine aminopeptidase, while the activity obtained at 37° C. is defined as 100.

As described above, the present invention relates to aminopeptidases from koji molds, nucleic acid molecules encoding them, transformed microorganism hosts harboring a recombinant DNA containing the nucleic acid molecules, and a process for producing an aminopeptidase by culturing the transformed microorganism hosts. In the present invention, an aminopeptidase protein from koji molds of the invention is represented by "PepE", and the gene encoding PepE is represented by "pepE". The term "aminopeptidase" as used herein indicates a protein having an activity of catalyzing the reaction for successively releasing amino acids from the N-terminal of a peptide.

The nucleic acid molecules encoding the aminopeptidases of the present invention can be obtained from the chromosomal DNA or cDNA of *Aspergillus nidulans*. Specifically, those nucleic acid molecules can be obtained from the chromosomal DNA library of *Aspergillus nidulans* such as *Aspergillus nidulans* A26. A clone harboring nucleic acid molecules of the present invention can be obtained by PCR (polymerase chain reaction) method using the chromosomal DNA library of *Aspergillus nidulans* as the template by producing PCR primers based on the gene sequence of aminopeptidase GX derived from germinating soybean (JP-Kokai No. 2000-325090) and the nucleotide sequences of EST fragments having a high homology in *Aspergillus nidulans* EST data base. The examples of PCR primers include, for example, oligonucleotides having the nucleotide sequence of SEQ ID NOs: 6 and 7.

The nucleic acid molecules of the present invention can be obtained from a cDNA library produced from poly (A) RNA of *Aspergillus nidulans* by PCR using oligonucleotides having the nucleotide sequence of SEQ ID NOs: 8 and 9 as primers, and by 5'-RACE using oligonucleotides of SEQ ID NOs: 10 and 11 as primers. SEQ ID NO: 1 shows the nucleotide sequence of genomic DNA containing the gene encoding *Aspergillus nidulans* A26 PepE obtained as described above. SEQ ID NO: 2 shows the nucleotide sequence and amino acid sequence of cDNA, and SEQ ID No: 3 shows the amino acid sequence thereof alone. The nucleotide sequences of genomic DNA and cDNA were compared with each other, which revealed that there were no introns in genomic DNA.

The nucleic acid molecules in the present invention may be those capable of encoding the aminopeptidases of the present invention. They include DNA containing the nucleotide sequence of nucleotide position Nos. 72 to 1628 of the nucleotide sequence shown in SEQ ID NO: 2 and also those obtained by removing an unnecessary part locating at the 5' terminal. The term "nucleic acid molecule" includes DNA, RNA and analogues of them. Depending on the purpose for which they are used, those encoding only mature protein are also usable. Nucleic acid molecules of the present invention also include those obtained by replacing a codon encoding an amino acid in the encoding domain with another equivalent codon. The nucleic acid molecules of the present invention may be those encoding aminopeptidase having the substitution, deletion, insertion, addition or inversion of one or more amino acids at one or plural positions so far as the encoded aminopeptidase activity is not impaired. The meaning of the term "plural", which varies depending on the position and variety of the amino acid residues in the three-dimensional structure of the peptidase protein, herein indicates usually 2 to 300, preferably 2 to 170, more preferably 2 to 50 and most preferably 2 to 10.

The nucleic acid molecule encoding the protein substantially the same as the aminopeptidase described above can be obtained by modifying the nucleotide sequence of pepE such that an amino acid at a particular position is substituted, deleted, inserted or added by, for example, a site-directed mutagenesis. The modified nucleic acid molecules can be obtained by a known process for mutagenesis. The processes for mutagenesis include a process where DNA encoding PepE is treated in vitro with hydroxylamine or the like and a process where *Escherichia* bacteria harboring DNA encoding PepE are irradiated with UV ray or treated with a mutagen usually used for the artificial mutagenesis such as N-methyl-N'-nitro-N-nitrosoguanidine (NTG) or nitrite.

The above-described substitution, deletion, insertion, addition or inversion of the nucleotide also includes the mutation naturally found in the varieties or strains of the koji mold. The nucleic acid molecule having such a mutation is expressed in suitable cells and PepE activity of the expressed product is examined to obtain nucleic acid molecules encoding the protein substantially the same as PepE. Further, nucleic acid molecules encoding the protein substantially the same as PepE protein can be obtained, for example, by isolating a nucleic acid molecules which can hybridize under stringent condition with a nucleic acid molecule having the sequence consisting of nucleotide no. 72 to 1628 of the nucleotide sequence of SEQ ID NO:2 and which encodes a protein having PepE activity. The term "stringent condition" herein indicates the condition under which so-called specific hybrids are formed. It is difficult to clearly numerate the conditions because they vary depending on GC content of each sequence and the presence or absence of repeated sequences. However, the conditions may be, for example, the condition where nucleic acid molecules having a high homology of, for example, at least 65%, can hybridize with each other and those having a homology of lower than 65% do not hybridize with each other. Alternately, the condition may be the one where such nucleic acid molecules hybridize under ordinary washing conditions for the Southern hybridization, i. e. 60° C., 1×SSC and 0.1% SDS, preferably 0.1×SSC and 0.1% SDS salt concentration. The genes which can hybridize under such conditions may contain those in which a stop codon is formed within the genes or those which lost the activity by a mutation in the active center. They can be easily removed by connecting them with a commercially available activity expression vector and determining PepE activity by a method which will be described below.

The nucleic acid molecules of the present invention can also be obtained from chromosomal DNA or cDNA of microorganisms of another species of the genus *Aspergillus* such as *Aspergillus oryzae*. In particular, they can be obtained from cDNA library of *Aspergillus oryzae* such as *Aspergillus oryzae* RIB40 (ATCC 42149) by PCR method. The nucleic acid molecules can be produced by synthesizing an oligonucleotide primer for PCR based on the nucleotide sequence of PepE of *Aspergillus nidulans* and conducting PCR by using cDNA library prepared from the cells of *Aspergillus oryzae*, e. g. *Aspergillus oryzae* RIB40, as the template. Primers for PCR include the oligonucleotides having the nucleotide sequences of SEQ ID NOs: 12 or 13 for 5'-RACE or the nucleotide sequences of SEQ ID NOs: 14 or 15 for 3'-RACE.

The nucleotide sequence and amino acid sequence of gene cDNA corresponding to pepE of *Aspergillus oryzae* RIB40 obtained as described above are shown in SEQ ID NO: 4 and the amino acid sequence is shown in SEQ ID NO: 5 alone. The amino acid sequence of PepE of *Aspergillus nidulans* shown in SEQ ID NO: 2 and the amino acid sequence of a corresponding aminopeptidase of *Aspergillus oryzae* shown in SEQ ID NO: 4 have a homology of about 77%, and furthermore, about 120 amino acid residues are different in the mature protein portions. The homology between pepE of *Aspergillus nidulans* and the corresponding gene of *Aspergillus oryzae* was about 71% for the coding region.

In one embodiment of the present invention, the nucleic acid molecule of the present invention comprises a nucleic acid molecule encoding a protein having an activity of catalyzing the reaction for releasing an amino acid from a peptide, wherein the protein has the amino acid sequence corresponding to amino acid position Nos. 1 to 510 of SEQ ID NO: 4 which have substitution, deletion, insertion, addition or inversion of one or more amino acids. In another embodiment, the nucleic acid molecules of the present invention include those that hybridize with DNA having a nucleotide sequence of nucleotide position Nos. 73 to 1602 in the nucleotide sequence of SEQ ID NO: 4 under stringent conditions and that encode a protein having an activity of catalyzing the reaction for releasing an amino acid from a peptide.

In Examples given below, the nucleic acid molecules of the present invention are the DNAs obtained as described above. Once the nucleotide sequences of them had been elucidated, it became possible to easily clone nucleic acid molecules encoding corresponding aminopeptidase from the genome DNA of *Aspergillus nidulans* A26, *Aspergillus oryzae* RIB40, or from other strains of *Aspergillus nidulans* or *Aspergillus oryzae* by PCR or hybridization. Accordingly, such nucleic acid molecules are within the scope of the present invention.

The nucleic acid molecules of the present invention are usable for producing the aminopeptidases of the present invention.

The nucleic acid molecules of the present invention are usable for breeding filamentous fungi such as koji mold or for producing aminopeptidase PepE. For example, in one embodiment of the present invention, PepE activity can be increased by introducing the DNA encoding aminopeptidase of the present invention into the cells of a filamentous fungus (such as *Aspergillus oryzae*), preferably as multi-copy DNA. PepE can be produced by expressing the nucleic acid molecules of the present invention in a suitable host. The filamentous fungi such as koji molds thus obtained or PepE obtained therefrom are usable for the production of soy sauce, miso (fermented soybean paste) and other seasonings containing protein hydrolysates.

The filamentous fungi into which the nucleic acid molecules of the present invention are introduced include the filamentous fungi belonging to the genus *Aspergillus* such as *Aspergillus oryzae*, *Aspergillus niger* and *Aspergillus nidulans*; those of the genus *Neurospora* such as *Neurospora crassa*; and those of the genus *Rhizomucor* such as *Rhizomucor miehei*. The filamentous fungi of the genus *Aspergillus* are particularly preferred.

The vectors for introducing the nucleic acid molecules of the present invention into the above-described filamentous fungi are not particularly limited and those usually used for breeding filamentous fungi are usable. For example, the vectors used for *Aspergillus oryzae* include pUNG (Lee, B. R. et al., Appl. Microbiol. biotechnol., 44, 425–431 (1995)), pMARG (Tsuchiya, K. et al., Appl. Microbiol. Biotechnol., 40, 327–332 (1993)), pUSC (Gomi, K. et al., Agric. Biol. Chem. 51, 2549–2555 (1987)), etc. pUNG has a marker complementing niaD- (defection in nitric acid assimilability) of *Aspergillus oryzae* niaD300 (Minetoki, T. et al., Curr. Genet. 30, 43214 438 (1996)); pMARG has a marker complementing argB- (arginine requirement) of *Aspergillus oryzae* M2-3 (Gomi, K. et al., Agric. Biol. Chem., 51(9), 2549–2555 (1987)); and pUSC has a marker complementing sC- (defection in ATP sulfurylase) of *Aspergillus oryzae* NS4 (Yamada, O. et al., Biosci. Biotech. Biochem., 61(8), 1367–1369 (1997)).

Among these vectors, pUNG and pMARG have a promoter for glucoamylase gene (glaA) and α-amylase gene (amyB terminator). By inserting the DNA of the present invention (for example, the region including nucleotide position Nos. 72 to 1628 of SEQ ID NO: 2) into the downstream of the promoter in frame, PepE can be expressed under the control of the promoter. When pUSC is used, since pUSC does not contain a promoter, PepE can be expressed by introducing it into the host filamentous fungus by the co-transformation thereof with a plasmid such as pUC19 containing DNA of the present invention inserted therein.

Vectors, promoters and markers described in literatures shown in Table 1 given below are also usable depending on the host filamentous fungus. In Table 1, the promoters are shown in terms of the enzymes encoded by the genes naturally regulated by the promoters.

TABLE 1

| Literature | Promoter | Marker | Host filamentous fungus |
|---|---|---|---|
| JP-Kokai No. 4-503450 | Neutral α-amylase | | *Aspergillus niger* |
| | | argB | *Aspergillus niger* |
| | | argB | *Aspergillus nidulans* |
| | | trpC | *Aspergillus nidulans* |
| | | amdS | *Aspergillus nidulans* |
| | | pyr4 | *Neurospora crassa* |
| | | DHFR | *Neurospora crassa* |

TABLE 1-continued

| Literature | Promoter | Marker | Host filamentous fungus |
|---|---|---|---|
| JP-Kokai No. 62-272988 | Taka-amylase Aspartic protease Lipase Glucoamylase, lipase Amylase, glucoamylase, cellulase Protease, glycolytic enzyme | | Aspergillus oryzae Rhizomucor miehei Rhizomucor miehei Aspergillus niger |
| JP-Kokai No. 7-51067 | Taka-amylase | | the genus Aspergillus |
| JP-Kokai No. 7-115976 | New promoter sequence is given | | Aspergillus oryzae |
| JP-Kokai No. 7-59571 | New promoter sequence is given | | Aspergillus oryzae |
| Nihon NougeiGakkaishi Vol. 71, No. 10 (1997) 1018–1023 | α-Amylase (anyB) Glucoamylase (glaA) Glucosidase (agdA) | | Aspergillus oryzae Aspergillus oryzae Aspergillus oryzae |

For transforming filamentous fungi, any well-known method can be employed in addition to the methods described in the literatures in Table 1. For example, *Aspergillus oryzae* can be transformed as described below.

The cells (conidia) are inoculated in DPY culture medium (2% of glucose, 1% of peptone, 0.5% of yeast extract, pH 5.0), and they are vigorously shaken at 30° C. for about 24 hours to conduct the shaking culture. The culture is filtered through Myracloth (CALBIO CHEM Co.) or a sterilized gauze or the like to recover the cells. The cells are washed with sterilized water and thoroughly drained. The cells are placed in a test tube. An enzyme solution [1.0% Yatalase; Takara Shuzo Co., Ltd.] or 0.5% NovoZyme (Novo Nordisk) and 0.5% cellulase (for example, Cellulase Onozuka; Yakult Co., Ltd.), 0.6 M of $(NH_4)_2SO_4$ and 50 mM of malic acid, pH 5.5] are added thereto and they are gently shaken at 30° C. for about 3 hours. The degree of the protoplastization is monitored with a microscope. When good condition is observed, the protoplasts are stored on ice.

The enzymatic reaction mixture is filtered through Myracloth to remove the cell residue. An equal amount of buffer A (1.2 M of sorbitol, 50 mM of $CaCl_2$, 35 mM of NaCl and 10 mM of Tris-HCl, pH 7.5) is added to the protoplast-containing filtrate, and the obtained mixture is placed in ice. After the centrifugation of the mixture at 1,500 to 2,500 rpm at 0° C. for 5 to 10 minutes, the centrifugation is slowly stopped. The pellets are washed with buffer A and then suspended in a suitable amount of buffer A. 20 μl or less of DNA solution (5 to 10 μg) is added to 100 to 200 μl of the protoplast suspension, and the obtained suspension is placed in ice for 20 to 30 minutes. 250 μl of buffer B (60% polyethylene glycol 6000, 50 mM of $CaCl_2$, 10 mM of Tris-HCl, pH 7.5) is added to the obtained mixture. After gentle mixing, additional 250 μl of buffer B is added thereto and the obtained mixture is gently mixed. Then 850 μl of buffer B is added to the mixture and they are gently mixed and then left to stand at room temperature for 20 minutes. 10 ml of buffer A is added to the mixture. The test tube is inverted to mix. After the centrifugation at 1,500 to 2,500 rpm at 0° C. for 5 to 10 minutes, the pellets are suspended in 500 μl of buffer A.

A suitable amount of the suspension thus obtained is added to 5 ml of the top agar which has been previously aliquoted and pre-warmed and was overlaid on the lower layer medium (selective medium prepared depending on the marker and containing 1.2 M of sorbitol), and cultured at 30° C. The grown cells are subcultured on the selection medium to confirm that they are transformants. It is preferred that recombinant DNA is further prepared from the cells to confirm the introduction of the DNA of the present invention by restriction enzyme analysis or Southern analysis and the like.

The transformants thus obtained are cultured under conditions suitable for the promoter used to express pepE and thereby to obtain PepE. For example, when *Aspergillus oryzae* is used as the host and glucoamylase promoter is used as the promoter, spores of transformed *Aspergillus oryzae* are suspended in a medium containing wheat bran, potassium phosphate, etc. and they are cultured at about 30° C. for about 3 days to produce PepE. If necessary, the culture is diluted with distilled water or the like and then extracted with a homogenizer or the like to obtain a crude enzyme extract containing PepE. The obtained crude extract can be treated by the gel filtration or a chromatography to further purify PepE. PepE thus obtained can be further purified by salting out, isoelectric precipitation, gel filtration, ion chromatography, reversed phase chromatography or the like and used for hydrolyzing proteins. It is also possible to obtain a protein hydrolysate having a high free amino acid content and a strong taste seasoning property by directly mixing a culture product of the transformed microorganism having an improved PepE activity obtained by the introduction of the nucleic acid molecules of the present invention with a proteinous starting material together with a proteolytic enzyme. The proteinous starting materials used herein are, for example, soybean, wheat and wheat gluten. They further include defatted soybean and various processed proteins such as swollen or solubilized proteins and also proteins separated from the various starting materials.

The activity of PepE can be determined by adding 0.02 ml of crude enzyme extract and 0.015 ml of 100 mM zinc chloride to 0.75 ml of 1 mM Leu-pNA (50 mM sodium phosphate buffer, pH 7.5), reacting them at 37° C. for 10 minutes, terminating the reaction by the addition of 0.25 ml of 40% acetic acid and determining the absorbance of the reaction solution at 405 nm. The activities of PepE in various preparations can be compared each other by defining the activity to generate 1 μmol of p-nitroanilide per minute as 1 unit (U) activity.

As for the practical conditions under which the cultured product of the transformed microorganism or crude enzyme is reacted on proteins, for example, a proteinous starting material having a concentration of 0.2 to 50% is mixed with the cultured product of the transformed microorganism in the presence of a proteolytic enzyme to conduct the reaction at 5 to 60° C. for 4 hours to 10 days.

After the completion of the reaction, insoluble matters such as the unreacted proteinous starting material and the cells are removed by an ordinary separation method such as the centrifugation or filtration. If necessary, the product can be concentrated under reduced pressure or by reverse osmosis or the like, and the concentrated product can be dried or granulated by a drying treatment such as freeze-drying, drying under reduced pressure or spray-drying. Thus, protein hydrolysates having a high free amino acid content and a strong taste seasoning property can be obtained.

EXAMPLES

Example 1

Cloning of pepE Genome DNA of *Aspergillus nidulans*

By homology searching using the EST database of *Aspergillus nidulans* on the basis of the sequence of aminopeptidase GX derived from germinating soybean, EST obd03a1.f1, which had a high homology, was found.

According to this information, *Aspergillus nidulans* pepE was cloned from *Aspergillus nidulans* genome library as follows.

The *Aspergillus nidulans* genome library was purchased from Fungal Genetics Stock Center (Kansas City, USA). This library had been obtained by cleaving the genomic DNA of *Aspergillus nidulans* with restriction enzymes, ligating the digest to a cosmid vector and introducing it into *Escherichia coli*. The library was screened as follows. *Escherichia coli* clones harboring the intended genes were screened by PCR using the oligonucleotides having the following sequences which had been synthesized according to the nucleotide sequence of EST obd03a1.f1 and *Escherichia coli* containing the cosmid vector as the source of template DNA.

```
(primer for 5' terminal)
CTC AAA CGG CCA CAT GAC TAC      (SEQ ID NO: 6)

(primer for 3' terminal)
GTC T GT TCA AGT GCA TAG CCT G   (SEQ ID NO: 7)

<sequence listing free text>
SEQ ID NOs: 6, 7: PGR primer
```

As for PCR reaction, 25 cycles of the reaction were conducted after the thermal denaturation at 94° C. for 3 minutes. Each cycle of the reaction was conducted at 94° C. for 30 seconds, at 52° C. for 10 seconds and at 72° C. for 30 seconds. As a result, it was elucidated that four clones contained the intended genes. The cosmid vectors were recovered from the clones to determine the nucleotide sequences. The nucleotide sequence and the amino acid sequence encoded by this nucleotide sequence are shown in SEQ ID NO: 2 and the amino acid sequence alone is shown in SEQ ID NO: 3.

*Escherichia coli* JM109 strain transformed with a plasmid obtained by inserting the gene into plasmid pUC19 was given a private number AJ13856 and deposited in National Institute of Bioscience and Human Technology, National Institute of Advanced Industrial Science and Technology Ministry of Economy, Trade and Industry (presently, National Institute of Advanced Industrial Science and Technology, Chuo No. 6, Higashi 1-1-1, Tsukuba-shi, Ibaraki-ken, Japan, 305–8566) on Mar. 19, 2001 to be preserved with nomination of FERM P-18263. On Mar. 11, 2002, this strain was transferred to the international deposit as FERM BP-7949.

Example 2

Cloning of pepE cDNA from *Aspergillus nidulans*

*Aspergillus nidulans* A26 was cultured by shaking in 50 ml of YG medium (0.5% of yeast extract, 2.5% of glucose, 0.1% of minor elements*, pH 6.5) at 30° C. for 48 hours (minor elements*: 0.1% of $FeSO_4.7H_2O$, 0.88% of $ZnSO_4.7H_2O$, 0.04% of $CuSO_4.5H_2O$, 0.015% of $MnSO_4.4H_2O$, 0.01% of $Na_2B_4O_7.10H_2O$, 0.005% of $(NH_4)_6 MoO_{24}.4H_2O$).

The cells were recovered, frozen in liquid nitrogen and crushed in a mortar. The total RNA was prepared from the crushed cells using RNeasy Plant Mini Kit (QIAGEN), and mRNA was prepared using Micro FAST Track Kit (Invitrogen). cDNA was synthesized from mRNA using cDNA Synthesis Kit (Promega), and the cDNA library was prepared with cDNA PCR Library Kit (TaKaRa).

By using the cDNA library as the template, pepE cDNA was cloned by PCR and 5'-RACE using the oligonucleotides, as the primers, which had the following sequences designed based on *Aspergillus nidulans* genomic DNA sequence.

```
(Primer for 5' terminal)
CAC CAC CAT GAG TCT AAC TTG G    (SEQ ID NO: 8)

(Primer for 3' terminal)
GTC TGT TCA AGT GCA TAG CCT G    (SEQ ID NO: 9)

(Primer for 5' terminal
for 5'-RACE)
CGT GGT ACC ATG GTC TAG AGT      (SEQ ID NO: 10)

(Primer for 3' terminal
for 5'-RACE)
AAT CGC AGT AAG CCT GCG AG       (SEQ ID NO: 11)

<Sequence listing free text>
SEQ ID NOs: 8–11: PCR primer
```

As for PCR reaction conditions, 30 cycles of the reaction were conducted after the thermal denaturation at 94° C. for 9 minutes. Each cycle of the reaction was conducted at 94° C. for 30 seconds, at 55° C. for 30 seconds and at 72° C. for 30 seconds, and finally the reaction was incubated at 72° C. for 5 minutes As a result, DNA fragments of about 1800 bp were obtained by PCR with primers of SEQ ID NOs: 8 and 9 and amplification fragments of about 250 bp were obtained by 5'-PACE with primers of SEQ ID NOs: 10 and 11. The nucleotide sequences of those DNA fragments and the amino acid sequences deduced from the nucleotide sequences are shown in SEQ ID NO: 2.

*Escherichia coli* JM109 strain transformed with the plasmid obtained by inserting the cDNA fragments of the above-described *Aspergillus nidulans* pepE into pBluescript was given a private number AJ13857 and deposited in National Institute of Bioscience and Human Technology, National Institute of Advanced Industrial Science and Technology Ministry of Economy, Trade and Industry (presently, National Institute of Advanced Industrial Science and Technology, Chuo No. 6, Higashi 1-1-1, Tsukuba-shi, Ibaraki-ken, Japan, 305–8566) as FERM P-18264 on Mar. 19, 2001 and was transferred to the International deposition On Mar. 11, 2002, as FERM BP-7950.

Example 3

Cloning of cDNA Homologous to *Aspergillus oryzae* pepE (1) Construction of *Aspergillus oryzae* cDNA Library

*Aspergillus oryzae* RIB40 (ATCC 42149) was cultured in 50 ml of DPY medium at 30° C. for 64 hours. The cells were harvested by filtration to recover 1 g thereof. The cells were immediately frozen in liquid nitrogen and crushed in a mortar. The total RNA was prepared from the crushed cells with RNeasy Plant Mini Kit (QIAGEN). Purified mRNA was obtained from the RNA with mRNA Purification Kit (Pharmacia), and the cDNA library was constructed using cDNA PCR Library Kit (TaKaRa) or 3'-RACE System for Rapid Amplification of cDNA Ends (GIBCO BRL).

(2) Screening of *Aspergillus oryzae* cDNA Library

The cloning of the cDNA homologous to *Aspergillus oryzae* pepE was conducted by 5'-RACE where oligonucleotides shown in SEQ ID NOs: 12 and 13 were used as the primers and also by 3'-RACE where those shown in SEQ ID NOs: 14 and 15 were used, considering the PepE sequence of *Aspergillus nidulans* obtained in Example 2.

```
(Primer for 5' terminal for
5'-RACE)
CGT GGT ACC ATG GTC TAG AGT       (SEQ ID NO: 12)

(Primer for 3' terminal for
5'-RACE)
CAT GGG CCC AAT GGT TCC GC        (SEQ ID NO: 13)

(Primer for 5' terminal for
3'-RACE)
CCA GAT TCG TAA TGA CTC CCG       (SEQ ID NO: 14)

(Primer for 3' terminal for
3'-RACE)

CTA CTA CTA CTA GGC CAC           (SEQ ID NO: 15)
GCG TCG ACT AGT AC
```

<Sequence listing free text>
SEQ ID NOs: 12–15: PCR primer

As for the PCR reaction of 5'-RACE, 35 cycles of the reaction was conducted after the thermal denaturation at 95° C. for 9 minutes. Each cycle of the reaction was conducted at 94° C. for 30 seconds, at 53° C. for 30 seconds and at 72° C. for 1 minute. As a result, *Aspergillus oryzae* pepE fragments of about 1400 bp were obtained. As for the PCR reaction of 3'-RACE, 35 cycles of the reaction was conducted after the thermal denaturation at 95° C. for 9 minutes. Each cycle of the reaction was conducted at 94° C. for 30 seconds, at 60° C. for 30 seconds and at 72° C. for 1 minute. As a result, the gene fragments of about 300 b analogous to *Aspergillus oryzae* pepE were obtained.

The nucleotide sequence of the gene fragments was determined to find that they contained the full length sequence homologous to that of pepE. The nucleotide sequence and the amino acid sequence encoded by this nucleotide sequence are shown in SEQ ID NO: 4 and the amino acid sequence alone is shown in ID NO: 5.

*Escherichia coli* DH5α strain transformed with a plasmid obtained by inserting the gene sequence into plasmid pBluescript was given a private number AJ13858 and deposited in National Institute of Bioscience and Human Technology, National Institute of Advanced Industrial Science and Technology Ministry of Economy (presently, Advanced Industrial Science and Technology, Chuo No. 6, Higashi 1-1-1, Tsukuba-shi, Ibaraki-ken, Japan, 305–8566) on Mar. 19, 2001 as FERM P-18265. On Mar. 11, 2002, this strain was transferred to the international deposit as FERM BP-7951.

Example 4

Expression of pepE in *Aspergillus oryzae*

(1) Preparation of Transformed *Aspergillus oryzae*

The pepE cDNA of *Aspergillus oryzae* obtained in Example 3 was ligated to pBluescript at the SmaI site to prepare plasmid pBSAopepE. pepE cDNA was excised from the plasmid with EcoRI and XbaI and then connected to the downstream of the glucoamylase promoter in pUNG1 vector containing niaD marker gene (Lee, B. R. et al., Applied Microbiology Biotechnology, 44, 425–431 (1995)) to obtain the plasmid pNGAPE, which was used for the transformation. The transformation was conducted with 10 μg of the plasmid DNA.

Conidia of *Aspergillus oryzae* niaD300 strain were inoculated in DPY culture medium. After shaking the culture at 30° C. for 24 hours, the culture mixture was filtered through sterilized gauze to recover the cells, which were then washed with sterilized water. The cells were placed in a test tube. 20 ml of an enzyme solution [1.0% Yatalase; (Takara Shuzo Co., Ltd.)] was added thereto and they are gently shaken at 30° C. for 3 hours. The degree of protoplastization was monitored under a microscope and then the protoplasts were stored in ice.

The enzymatic reaction mixture was filtered through Myracloth to remove the cell residue. An equal amount of buffer A (1.2 M of sorbitol, 50 mM of $CaCl_2$, 35 mM of NaCl and 10 mM of Tris-HCl, pH 7.5) was added to the protoplast-containing filtrate, and the obtained mixture was placed in ice. After the centrifugation of the mixture at 1,500 rpm at 0° C. for 5 minutes, the centrifugation was slowly stopped. The pellets were washed with 10 ml of buffer A twice and then suspended in 1 ml of buffer A.

10 μl of DNA solution (10 μg) was added to 100 μl of the protoplast suspension, and the obtained mixture was placed on ice for 30 minutes. 250 μl of buffer B (60% PEG (polyethylene glycol) 6000, 50 mM of $CaCl_2$, 10 mM of Tris-HCl, pH 7.5) was added to the obtained mixture. After gently mixing, additional 250 μl of buffer B was added thereto and the obtained mixture was gently mixed. Then 850 μl of buffer B was added to the mixture and they are gently mixed and left to stand at room temperature for 20 minutes. Then, 10 ml of buffer A was added to the mixture. The test tube was inverted. After the centrifugation at 1,500 rpm at 0° C. for 5 minutes, the pellets were suspended in 500 μl of buffer A.

The suspension thus obtained was added to 5 ml of top agar medium which had been previously aliquoted and pre-warm and overlaid on Czapek Dox medium (1.2 M of sorbitol, 0.3% of sodium nitrate, 0.2% of potassium chloride, 0.1% of potassium phosphate, 0.05% of magnesium sulfate heptahydrate, 0.002% of ferrous sulfate heptahydrate and 2% of glucose, pH 5.5), and they were cultured at 30° C. Ten strains of the grown cells were inoculated on Czapek Dox medium to obtain the stable transformants.

(2) Production of pepE

The transformant obtained as described above was cultured with wheat bran, and the aminopeptidase activity of the extract obtained therefrom was determined.

20 g of wheat bran, 0.3 g of potassium phosphate and 14 ml of distilled water were thoroughly stirred together. The obtained mixture was placed in an Erlenmeyer flask and autoclaved at 120° C. for 30 minutes to produce a medium. 8 ml of sterilized water was poured into a petri dish, in which a plenty of the spores were formed, and they were stirred together to prepare a spore suspension. The spore suspension was sprayed on the medium. The medium on which the spores were inoculated was thoroughly stirred. After culturing at 30° C. for 3 days, 10 parts of distilled water was added to 1 part of the wheat bran prepared as described above and they were extracted with a homogenizer for 5 minutes to obtain a crude enzyme extract.

The aminopeptidase activity of the crude enzyme extract prepared as described above was determined as follows: 0.02 ml of the crude enzyme extract and 0.015 ml of 100 mM zinc chloride were added to 0.75 ml of 1 mM Leu-pNA (50 mM sodium phosphate buffer, pH 7.5) to conduct the reaction at 37° C. for 10 minutes. 0.25 ml of 40% acetic acid was added to the reaction mixture to terminate the reaction. The absorbance of the reaction mixture at 405 nm was measured to determine the activity. 1 unit (U) of the enzymatic activity was defined as the activity forming 1 μmol of p-nitroanilide per minute. As a control, a crude enzyme extract was prepared from a transformant obtained by the transformation with vector DNA containing only the marker gene, and the aminopeptidase activity thereof was determined by the same method as that described above.

As a result, a remarkable increase in the aminopeptidase activity was recognized with the strain in which the gene of the present invention was introduced (Table 2). It was thus confirmed that the introduced aminopeptidase gene was actually expressed and that the aminopeptidase was produced.

TABLE 2

Aminopeptidase activity in crude enzyme extract

|  | Aminopeptidase activity (per mg of protein) |
|---|---|
| Transformant strain 1 | 0.09 U |
| Transformant strain 2 | 0.10 U |
| Transformant strain 3 | 0.12 U |
| Transformant strain 4 | 0.09 U |
| Transformant strain 5 | 0.11 U |
| Control strain 1 | 0.03 U |
| Control strain 2 | 0.02 U |
| Control strain 3 | 0.03 U |

Example 5

Characterization of PepE (1) Purification of pepE 20 g of wheat bran medium was placed in a 300 ml flask and then autoclaved at 120° C. for 20 minutes to prepare a medium.

The spore suspension was prepared for the transformant highly expressing PepE prepared in Example 4. The suspension was inoculated in the medium, thoroughly mixed and cultured at 30° C. for 5 days. During the culture, 48 hours after the start of the culture the medium was cared by stirring.

1 part (w/w) of the wheat bran thus obtained was immersed in a mixture of 10 parts (w/w) of 20 mM potassium phosphate buffer (pH 7.4), 1 mM EDTA and 1 mM PMSF (phenyl methane sulfonyl fluoride). After leaving the obtained mixture to stand at 4° C. for 16 hours, the reaction mixture was filtered through a gauze and then centrifuged (7,500 rpm, 4° C., 10 minutes) to obtain a supernatant liquid to be used as a crude enzyme extract.

Ammonium sulfate was added to the crude enzyme extract to obtain 40%–60% ammonium sulfate precipitation fraction. The precipitate was dissolved in 20 mM potassium phosphate buffer (pH 7.4). The obtained solution was filtered through a filter having a pore diameter of 0.45 μm. The filtrate was applied to a desalting column [HiTrap Desalting of Amersham Pharmacia (25 ml)] previously equilibrated with 20 mM potassium phosphate buffer (pH 7.4) and 150 mM NaCl and eluted with the same buffer. The obtained active fraction was concentrated by ultrafiltration.

The sample thus obtained was adsorbed on an anion exchange column [HiTrap Q-sepharose HP of Amersham Pharmacia (25 ml)] previously equilibrated with 20 mM potassium phosphate buffer (pH 7.4), and then washed with the same buffer in an amount of 3 volumes of the column volume. After the completion of the washing, the active fraction was eluted by linearly increasing NaCl concentration of the buffer from 0 M to 1 M in 20 volumes of the column volume to conduct the elution. The active fraction recovered in the effluent was concentrated by ultrafiltration.

The obtained sample was fractionated by the gel filtration chromatography with HiLoad 26/60 Superdex 200 pg (Amersham Pharmacia). The sample was applied to the column previously equilibrated with 20 mM potassium phosphate buffer (pH 7.4) and 150 mM NaCl and the active fraction was recovered by the elution with the same buffer. Thus, purified PepE was obtained after these procedures.

(2) Determination of PepE Activity

The aminopeptidase activity of the enzyme extract was determined as follows. 0.02 ml of the crude enzyme extract was added to 0.73 ml of a substrate solution (1 mM Leu-pNA, 50 mM sodium phosphate buffer (pH 7.5), 2 mM cobalt chloride). After conducting the reaction at 37° C. for 10 minutes, 0.25 ml of 40% acetic acid was added to the reaction mixture to terminate the reaction. The absorbance of the reaction solution at 405 nm was determined and the activity was calculated therefrom. An enzymatic activity for forming 1 μmol of p-nitroanilide per minute was defined as 1 unit.

The enzymatic properties of this enzyme are as follows.

(i) Substrate Specificity

The hydrolyzing activities for various X-pNA were determined by the above-described method for determining the activity except that Leu-pNA was replaced with X-pNA. The obtained relative activities, on the basis of the activity for Leu-pNA as 100, are shown in Table 3 given below. It was elucidated that this enzyme efficiently hydrolyzed the peptides having Leu at the N-terminal thereof.

TABLE 3

Substrate specificity of PepE

| X-pNA | X | | | | | | | | | | |
|---|---|---|---|---|---|---|---|---|---|---|---|
|  | Leu | Lys | Met | Asp | Phe | Arg | Val | Ile | Pro | Gly | Glu | Ala |
| Relative value | 100 | 0 | 26 | 0 | 2 | 0 | 1 | 1 | 0 | 1 | 0 | 1 |

(ii) Optimum Temperature

LAP activity was determined at a various temperature by the above-described method for determining the activity. The obtained relative activities, on the basis of the activity at 37° C. as 100, are shown in FIG. 1.

(iii) Effects of Sodium Chloride Concentration in the Reaction Solution

Figure 2:
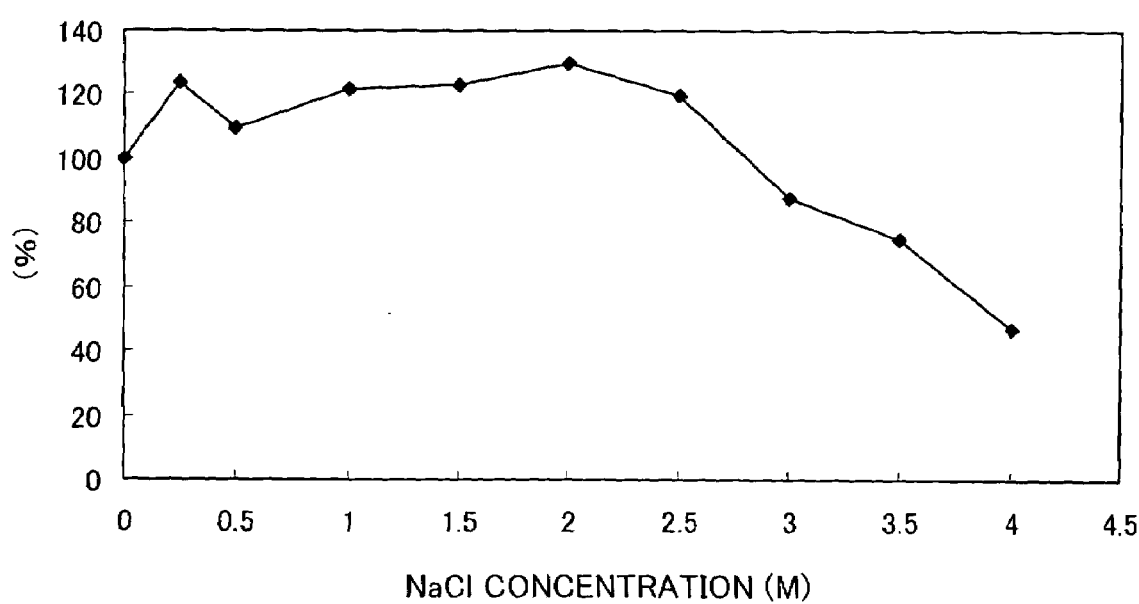
FIG. 2 is a graph showing the influence of the concentration of sodium chloride in the reaction mixture on PepE. The horizontal axis shows NaCl concentration (M), and the longitudinal axis shows the relative activity of leucine aminopeptidase at varied NaCl concentration, while the activity in the absence of NaCl is defined as 100.

LAP activity obtained by adding varied concentration of NaCl was determined by the above-described method for determining the activity. The relative activities, on the basis of the activity in the absence of NaCl as 100, are shown in FIG. 2. It was apparent that the enzyme was capable of retaining its activity even in the presence of a high concentration of sodium chloride.

(iv) Optimum pH

Figure 3:
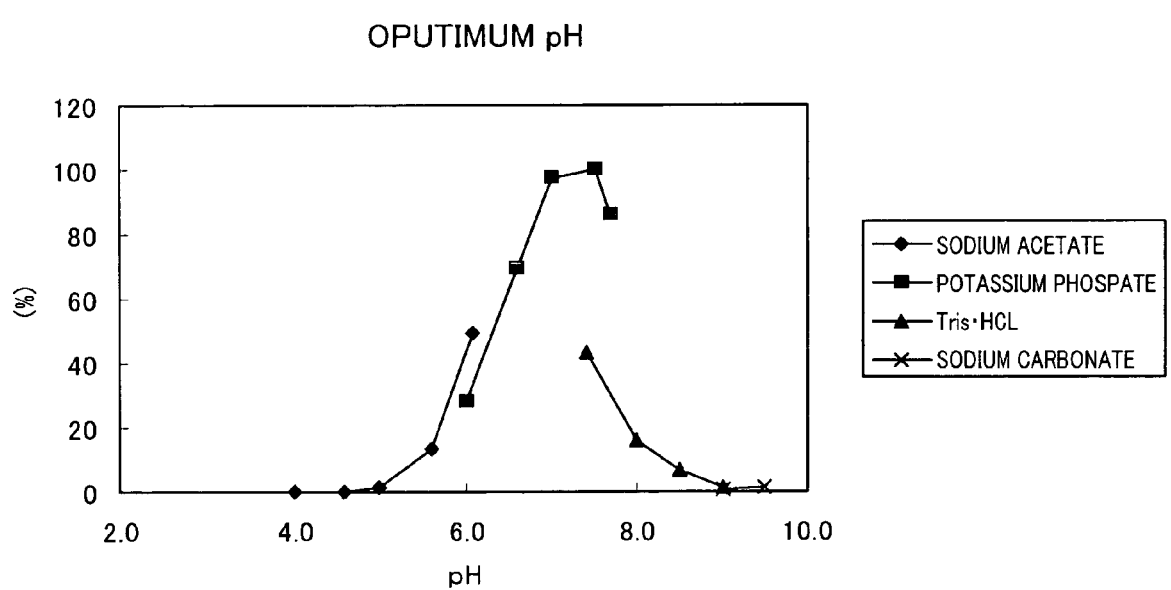
FIG. 3 is a graph showing the dependence of PepE activity on pH. The horizontal axis represents pH, and the longitudinal axis represents the relative activity of leucine aminopeptidase, while the activity in a potassium phosphate buffer (pH 7.5) is 1 defined as 100.

The above-described activity determination method was repeated except that 50 mM sodium phosphate buffer (pH 7.5) was replaced with another pH buffer so that the final concentration thereof would be 50 mM. The LAP activity in potassium phosphate buffer (pH 7.5) was defined to be 100. The activity at each pH is shown in FIG. 3.

(v) pH Stability

The purified enzyme was kept in 50 mM buffers having various pH at 0° C. for 24 hours and then LAP activity was determined by the above-described activity determination method (pH 7.5). The relative activities, determined on the basis of the activity (100) after the storage in the phosphate buffer of pH 7.5, are shown in Table 4.

TABLE 4 pH Stability of PepE

| Buffer | pH | Relative activity (%) |
|---|---|---|
| Sodium acetate | 4.7 | 18 |
| Sodium acetate | 5.8 | 157 |
| Potassium phosphate | 6.4 | 145 |
| Potassium phosphate | 7.0 | 100 |
| Potassium phosphate | 7.5 | 100 |
| Tris | 8.0 | 88 |
| Sodium carbonate | 8.8 | 82 |
| Sodium carbonate | 9.5 | 64 |

(vi) Stability in Sodium Chloride Solution

The purified enzyme was kept in 0–4 M NaCl, 20 mM phosphate buffer (pH 7.5) at 0° C. for 24 hours and then the activity thereof in the reaction mixture having a salt concentration equal to the storage salt concentration was determined. The results are shown in Table 5.

TABLE 5

Stability of PepE in sodium chloride solution

| Salt concentration (M) | Relative activity (%) |
|---|---|
| 0 | 100 |
| 1 | 85 |
| 2 | 107 |
| 3 | 84 |

(vii) Effects of Metal Ion

The hydrolyzing activity for various X-pNA was determined by the above-described activity determination method except that cobalt chloride was replaced with various divalent metal salts. The relative activity is shown in Table 6 in which the hydrolyzing activity of Leu-pNA in the presence of cobalt chloride is defined as 100.

TABLE 6

Effects of metal ion on PepE activity

| $XCl_2$ | Relative activity (%) |
|---|---|
| X = $Co^{++}$ | 100 |
| X = $Ni^{++}$ | 1 |
| X = $Mn^{++}$ | 1 |
| X = $Mg^{++}$ | 1 |
| X = $Cu^{++}$ | 1 |
| X = $Ca^{++}$ | 1 |
| X = $Zn^{++}$ | 11 |
| No additive | 2 |

The present invention provides a means for obtaining a protein hydrolysate having a high free amino acid content and a strong seasoning property. In particular, the present invention provides an aminopeptidase capable of efficiently hydrolyzing peptides in the production of soy sauce having a high sodium chloride content by the fermentation and also a nucleic acid encoding the same. By the present invention, the seasoning property of soy sauce or protein hydrolysates can be further improved.

The hosts containing the nucleic acid molecule of the present invention in a form, which allows the expression of the nucleic acid molecule, are usable for producing the protein of the present invention.

What is claimed is:

1. An isolated protein selected from the group consisting of
   (i) a protein comprising the amino acid sequence of SEQ ID NO:5, and
   (ii) a protein wherein the amino acid sequence of SEQ ID NO:5 comprises a substitution, or deletion, or insertion of no more than ten amino acids and retains the activity of catalyzing the reaction for liberating an amino acid at an N-terminal of a peptide.

2. An isolated *Aspergillus oryzae* aminopeptidase having each of the following properties:
   1) hydrolyzing a peptide or protein having leucine or methionine at the N-terminal to release leucine or methionine;
   2) having an optimum pH of 7.0 to 7.5;
   3) having an optimum temperature of 37° C. to 45° C.;
   4) having a remaining activity of at least 80% even at a sodium chloride concentration of 3M, with the activity thereof in the absence of sodium chloride being defined as 100%;
   5) having a remaining activity of at least 80% after storage in the presence of 3M sodium chloride at 0° C. for 24 hours, with the activity thereof after storage in the absence of sodium chloride at 0° C. for 24 hours being defined as 100%;
   6) having a remaining activity of at least 60% after storage at pH 5.8 to 9.5 at 0° C. for 24 hours, with the activity thereof after storage at pH 7.5 at 0° C. for 24 hours being defined as 100%;
   7) having a molecular weight of 550 kD as measured on a native PAGE gel and a molecular weight of 22 or 33 kD as measured on a SDS-PAGE gel after reducing and heating said protein; and,
   8) requiring cobalt ion or zinc ion for being activated.

3. An isolated polynucleotide encoding a protein selected from the group consisting of
   (i) a protein comprising the amino acid sequence of SEQ ID NO:5, and
   (ii) a protein wherein the amino acid sequence of SEQ ID NO:5 comprises a substitution, or deletion, or insertion of no more than ten amino acids and retains the activity of catalyzing the hydrolysis of an amino acid from the N-terminal of a peptide.

4. The isolated polynucleotide according to claim 3, which is selected from the group consisting of
   (i) a DNA comprising the sequence of nucleotides from position 73 to position 1602 set forth in SEQ ID NO:4, and
   (ii) a DNA that hybridizes with the DNA of clause (I) under stringent conditions and that encodes a protein having the activity of catalyzing the hydrolysis of an amino acid from the N-terminal of a peptide, wherein said stringent conditions comprise a washing step at 60° C. in 1×SSC and 0.1% SDS.

5. The isolated polynucleotide according to claim 4 having the nucleotide sequence of SEQ ID NO:4.

6. A recombinant polynucleotide that comprises the polynucleotide according to claim 3.

7. An isolated transformed microorganism host cell that comprises the polynucleotide according to claim 3 in a form that can be expressed.

8. The isolated transformed microorganism host cell according to claim 7, which is a filamentous fungus, a yeast, or an *Escherichia* bacterium.

9. A process for producing an aminopeptidase, which comprises culturing the isolated transformed microorganism host cell according to claim 8 to express the protein encoded by the polynucleotide introduced into the transformed microorganism host cell and recovering the produced protein.

* * * * *